(12) United States Patent
Spaeth et al.

(10) Patent No.: US 8,042,946 B1
(45) Date of Patent: Oct. 25, 2011

(54) CONTRAST SENSITIVITY TEST

(76) Inventors: George L. Spaeth, Philadelphia, PA (US); Jesse Richman, Providence, RI (US)

( * ) Notice: Subject to any disclaimer, the term of this patent is extended or adjusted under 35 U.S.C. 154(b) by 0 days.

(21) Appl. No.: 12/799,028

(22) Filed: Apr. 16, 2010

(51) Int. Cl.
*A61B 3/02* (2006.01)

(52) U.S. Cl. ................................................. 351/239

(58) Field of Classification Search ........... 351/239–245
See application file for complete search history.

(56) References Cited

U.S. PATENT DOCUMENTS

| 6,379,007 B1 * | 4/2002 | Farb | 351/239 |
| 7,697,212 B2 * | 4/2010 | Jethmalani et al. | 359/652 |

* cited by examiner

*Primary Examiner* — William C Choi
*Assistant Examiner* — Tuyen Tra
(74) *Attorney, Agent, or Firm* — Scully, Scott, Murphy & Presser, P.; Steven I. Wallach

(57) ABSTRACT

Methods and apparatus are provided for measuring contrast sensitivity. In one method, a person is presented with a test pattern having several test areas. In a first test cycle, one of the test areas contrasts with (for example, is darker than) the other test areas. The person being tested indicates which test area the person perceives as contrasting with (darker than) the other test areas. This is repeated a number of times for the other test areas, with the level of contrast staying the same but with a different test area becoming the contrasting (darker) test area. In subsequent cycles, these steps are repeated, with decreasing levels of contrast. The contrasting test area may, for example, appear as a solid, as a pattern such as two contrasting vertical bars, or as an animation such as a sinusoidal frequency grating.

42 Claims, 9 Drawing Sheets

CONTRAST SENSITIVITY TEST

BACKGROUND OF THE INVENTION

1. Field of the Invention

This invention relates generally to testing vision, in particular to testing contrast sensitivity.

2. Background

A number of qualities or functions are used to describe how good a person's eyesight is. One such function is "visual acuity," which can be described as the ability to resolve or distinguish details of objects, as determined by the smallest object that a person can identify at a specified distance. Visual acuity can be measured by what many people think of as the most common eye test: reading with one eye at a time a chart having several lines of letters, typically with one large letter (such as a capital "E") on the top line, and additional lines having an increasing number of letters that decrease in size. Normal visual acuity is generally referred to as 20/20 vision, meaning that a particular person sees clearly at 20 feet what humans can normally see clearly at 20 feet. Someone with 20/40 vision can see clearly at 20 feet what people normally can see clearly at 40 feet.

Another aspect of eyesight or vision is the "visual field" or "field of vision," which can be described as where a person can see, or the full extent of the area visible to an eye that is fixed, or fixating, straight ahead. Visual field is usually expressed as angles measured in degrees from a point of fixation. Horizontally, normal visual field from a point of fixation is about 95 degrees toward a person's temple and about 60 degrees toward a person's nose; vertically, normal visual field is about 50 degrees above and 65 degrees below the point of fixation.

Yet another visual function is "contrast sensitivity," which can be described as the ability to see a difference in contrast between an image and the background of an image. For example, black writing on a white billboard normally presents a high contrast that someone with normal vision can see easily. On a very foggy day, the black writing and the white background can appear grayish and be more difficult to see. Someone with good contrast sensitivity might be able to see the writing on the billboard well enough to read it through the fog, while someone else with poor contrast sensitivity may be unable to do so.

In addition, contrast sensitivity is fundamental to visual acuity and visual field. Thus, contrast sensitivity is increasingly recognized as an important, perhaps the most important, visual function in determining how well individuals can perform the activities of daily living such as reading, doing housework, watching television, and getting around from place to place. This makes tests for contrast sensitivity increasingly important.

But previously known methods of testing contrast sensitivity exhibit several disadvantages. Tests in which a person is asked to read letters (e.g., the Pelli Robson test) depend upon the person's ability to resolve objects—that is, the person's visual acuity. For individuals with poor visual acuity, such tests have a decreased ability to determine contrast sensitivity. For example, certain eye diseases, such as macular degeneration, affect the central portion of the eye's retina, which is where resolution is highest and is used in activities such as reading. Thus, for someone afflicted with such an eye disease, a test for contrast sensitivity that includes reading letters will be confounded by relying heavily on resolution (i.e., visual acuity), thus providing an inaccurate measure of contrast sensitivity. In addition, such a contrast sensitivity test may be difficult or impossible to administer to illiterate persons.

Some other previously known contrast sensitivity tests ask a person to stare at a fixed point while small bursts of light (or similar illumination or animation) appear in the person's peripheral vision. For example, a person may be asked to stare at a fixed point on a computer screen while small, animated "bursts" are displayed at various peripheral points on the screen. But such contrast sensitivity test tests depend on the person's visual field: for individuals with constricted visual fields, such tests have a decreased ability to determine contrast sensitivity. For example, certain eye diseases, such as glaucoma, can affect peripheral vision. Therefore, for someone afflicted with such an eye disease, a test for contrast sensitivity that includes peripheral bursts of illumination will be confounded by relying heavily on visible area (i.e., visual field), again providing an inaccurate measure of contrast sensitivity.

SUMMARY OF THE INVENTION

In one embodiment of the invention, a method for measuring contrast sensitivity includes presenting to a person a test pattern having two or more test areas. The method further includes providing that one of the test areas contrasts with the other test areas and receiving a response from the person indicating which test area the person perceives as contrasting with the other test areas. These steps are repeated a number of times, each time providing that another test area contrasts with the other test areas. The preceding steps are then repeated another number of times, each time decreasing the contrast that appears between the test areas.

In another embodiment of the invention, one of the contrasting test areas appears as a solid. In still another embodiment, one of the contrasting test areas appears as a pattern. In still another embodiment, the pattern is two or more contrasting brightnesses. In still another embodiment the contrasting test area appears as an animation. In still another embodiment the animation is a sinusoidal frequency grating.

In yet another embodiment of the invention, a method for measuring contrast sensitivity includes presenting to a person a test pattern having two or more test and nontest areas. The method further includes providing that one of the test areas contrasts with the other test and nontest areas and receiving a response from the person indicating which test area the person perceives as contrasting with the other test and nontest areas. These steps are repeated a number of times, each time providing that another test area contrasts with the other test and nontest areas. The preceding steps are repeated another number of times, each time decreasing the contrast that appears between one of the test areas and the other test and nontest areas.

In yet another embodiment of the invention, a method for measuring contrast sensitivity includes presenting to a person a test pattern including five test areas. The method further includes providing that one of the test areas contrasts with the other four test areas and receiving a response from the person indicating which test area the person perceives as contrasting with the other test areas. These steps are repeated at least four more times, each time providing that another test area contrasts with the other test areas and that no test area repeats as the contrasting test area. The preceding steps are then repeated up to 20 times, each time decreasing the contrast that appears between the test areas.

In yet another embodiment of the invention, the test pattern is a 3 by 3 matrix, and in row 1, columns 1 and 3 are test areas and column 2 is a nontest area; in row 2, column 2 is a test area and columns 1 and 3 are nontest areas; and in row 3, columns 1 and 3 are test areas and column 2 is a nontest area.

In yet another embodiment of the invention, a method for measuring contrast sensitivity includes presenting to a person a test pattern having a plurality of test areas. The method further includes providing that one of the test areas has a first brightness and that the other test areas have a second brightness—with the first brightness darker than the second brightness—and receiving a response from the person indicating which test area the person perceives as darker than the other test areas. These steps are repeated a number of times, each time providing that another test area is darker than the remaining test areas. The preceding steps are then repeated another number of times, each time decreasing the contrast between the darker test area and the other test areas.

DETAILED DESCRIPTION OF PREFERRED EMBODIMENTS

Figure 1:
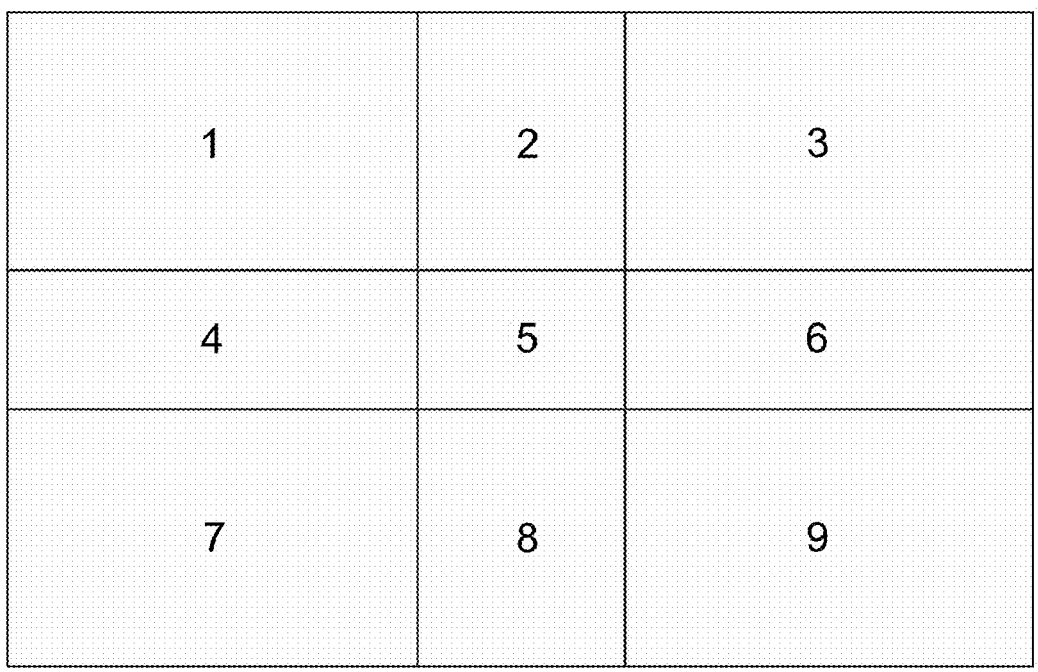
FIG. 1 is a computer screenshot depicting a test pattern, or test panel, according to one embodiment of the invention.

FIG. 1 depicts a test pattern, or test panel, in accordance with one embodiment of the invention. A test area 5 in the center of the test pattern is substantially square. Four test areas are disposed around test area 5: upper left-hand corner 1, upper right-hand corner 3, lower left-hand corner 7, and lower right-hand corner 9 (which may be referred to as test areas 1, 3, 7, and 9 respectively). Horizontal bands 4 and 6 extend from test area 5 to the left and right edges, respectively, of the test pattern. Vertical bands 2 and 8 extend from test area 5 to the top and bottom edges, respectively, of the test pattern. Bands 2, 4, 6, and 8 serve to separate the test areas from each other (except where test areas 1, 3, 7, and 9 meet the corners of test area 5) and may be referred to as nontest areas 2, 4, 6, and 8, respectively. Any of areas 1-9 may also be loosely referred to as a quadrant.

FIG. 1 may also be described as consisting of a 3 by 3 matrix. Considering the rows from top to bottom and the columns from left to right: in row 1, columns 1 and 3 are test areas and column 2 is a nontest area; in row 2, column 2 is a test area and columns 1 and 3 are nontest areas; and in row 3, columns 1 and 3 are test areas and column 2 is a nontest area.

A test session for measuring contrast sensitivity using the test pattern of FIG. 1 includes a number of cycles. In any one cycle, there is a level of contrast between the quadrants. Preferably, one quadrant is relatively dark and the other eight quadrants are relatively light. With each successive cycle the brightness (darkness or lightness) of one or more of the quadrants will change, such that there is a change (preferably a decrease) in the level of contrast between the relatively dark quadrant(s) and the relatively light quadrant(s).

Each cycle consists of one or more sets of displays that use variations of the test pattern of FIG. 1, with one or more quadrants darker than one or more other quadrants. One example of a cycle consisting of six display sets is shown in FIG. 2, with the next two cycles shown in FIGS. 3 and 4. In this example, one test area is darker than the other eight quadrants; with each successive cycle the darker test area will become lighter, while all other quadrants of the test panel will become darker. Thus with each successive cycle the contrast between the darker test area and the other quadrants decreases. One preferred test session consists of up to 20 cycles.

To help establish a fixation point for the person being tested while he or she is looking at the display, one of the test areas—preferably test area 5—may include a letter, number, symbol, ideogram, icon, sign, shape, figure, picture, or any other image. Preferably the image used is a single letter (although multiples or combinations of images could be used) and may change or repeat with each display set. (For example, the image used may be selected randomly or in a predetermined sequence from the 26 letters A-Z.) With this flexibility, the patient may be literate in any language, or illiterate. Also preferably included are the crossing lines shown, for example, in FIG. 1—horizontally below row 1 and above row 3, and vertically to the right of column 1 and to the left of column 3—to provide guidance to assist fixation, with the person being tested instructed to keep looking at the area in the center where all the lines cross.

Example # 1

One preferred test session, in which the dark test area appears as a solid, proceeds as follows. As shown in FIG. 2, in the first cycle one brightness value $B_D$ for a dark test area is set to a darkest value (e.g., absolute black) and another brightness value $B_L$ for the other, relatively light quadrants is set to a least-dark value (e.g., absolute white) for use during the session. The first display set will have one test area dark and the other eight quadrants light; in the subsequent display sets, the test area that had been dark will become light and another of the other four test areas will become dark, with no test area repeating as the dark area. The sixth display set repeats one of the earlier display sets in the cycle so that the patient cannot deduce which test area will next be dark. For each of the first five display sets, the test area that is dark may be predetermined (for example, by a software-programmed sequence) or may be determined randomly, so long as no test area is dark a second time. The repeated sixth display set also may be predetermined (for example, by a software-programmed selection) or may be determined randomly.

Specifically, for the six display sets shown in FIGS. 2A-2F: in the first set test area 7 is dark; in the second set test area 3 is dark; in the third set test area 5 is dark; in the fourth set test area 1 is dark; in the fifth set test area 9 is dark; and the sixth set repeats the fourth set. In each of these display sets, the dark test area is at a darkest value ($B_D$=absolute black) and the other test areas and the other eight quadrants are at a lighter value ($B_L$=absolute white).

In subsequent cycles, there is a progressively lower contrast between the relatively dark test area and the eight other quadrants that are relatively light. Preferably, at the start of each subsequent cycle, the brightness value $B_D$ (for the dark test areas) is set to a less-dark value than in the previous cycle, while the brightness value $B_L$ (for the light quadrants) is set to a more-dark value than in the previous cycle. Accordingly, FIG. 3 depicts a second cycle, with six display sets shown in FIGS. 3A-3F: in the first set test area 1 is dark; in the second set test area 5 is dark; in the third set test area 9 is dark; in the fourth set test area 7 is dark; in the fifth set test area 3 is dark; and the sixth set repeats the second set. In each of these display sets, the dark test area is at a less-dark value compared with that in the first cycle (e.g., $B_D$=98% of absolute black) and the other quadrants are at a less-lighter value compared with that in the first cycle (e.g., $B_L$=10% of absolute black). In an alternative example, the other quadrants remain at the same value as in the first cycle (e.g., $B_L$=absolute white).

FIG. 4 depicts the third cycle, with six display sets shown in FIGS. 4A-4F: in the first set test area 9 is dark; in the second set test area 3 is dark; in the third set test area 1 is dark; in the fourth set test area 5 is dark; in the fifth set test area 7 is dark; and the sixth set repeats the first set. In each of these display sets, the dark test area is at a less-dark value compared with that in the second cycle (e.g., $B_D$=95% of absolute black) and the other quadrants are at a less-lighter value compared with that in the second cycle (e.g., $B_L$=15% of absolute black). In an alternative example, the other quadrants remain at the same value as in the first cycle (e.g., $B_L$=absolute white).

Example # 2

In a second example of a test session according to the invention, contrast decreases in each cycle by having the light areas get gradually darker. Again, in this test session's first cycle, one brightness value $B_D$ is set to a darkest value (e.g., absolute black) and another brightness value $B_L$ is set to a least-dark value (e.g., 10% of absolute black) for use during the session. In the first cycle, one test area in each display set will be dark ($B_D$=absolute black) and the other four test areas will be light ($B_L$=absolute white). But at the start of each subsequent cycle, the first value remains constant ($B_D$=absolute black), while the second value is set to a higher darkness value than in the previous cycle (e.g., in cycle No. 2, $B_L$=15% of absolute black; in cycle No. 3, $B_L$=18% of absolute black, and so on).

Example # 3

In a third example of a test session according to the invention, in which the dark test area appears as an animation of a sinusoidal frequency grating, display sets include no letter or other image in test area 5, as shown in FIG. 5. In addition, in the first cycle, one test area will contain vertical bars of two contrasting shades of gray, with the other test areas being the lighter of the two shades. In each display set as shown in FIGS. 5A-5F, the test area that contains the contrasting vertical bars preferably undergoes the following animated transition: it will first appear as a solid gray tone throughout the given test area, then for approximately ⅓ of a second it will appear as the contrasting grayscale bars, the lighter of the grayscales being the same shade as seen in the initial solid gray tone, then it will revert to the initial solid gray tone and remain that way until a mouse click is made.

Example # 4

Figure 6A:
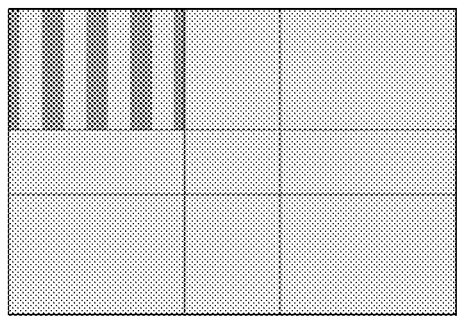
FIGS. 6A-F are computer screenshots depicting an example of a first cycle in a test session according to yet another embodiment of the invention.
Figure 6B:
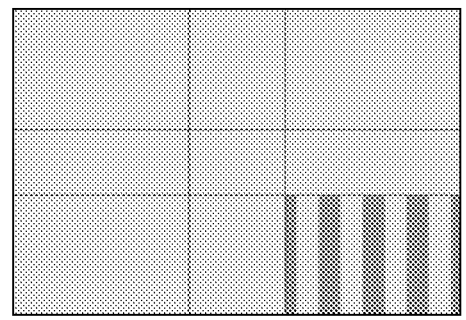
Figure 6C:
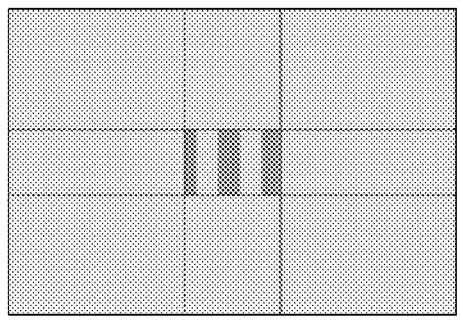
Figure 6D:
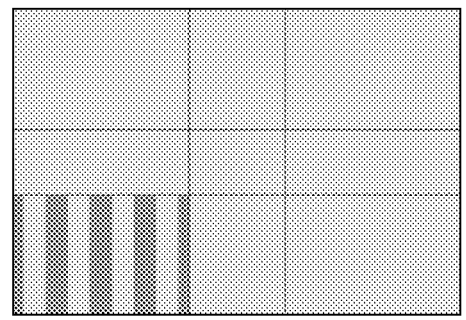
Figure 6E:
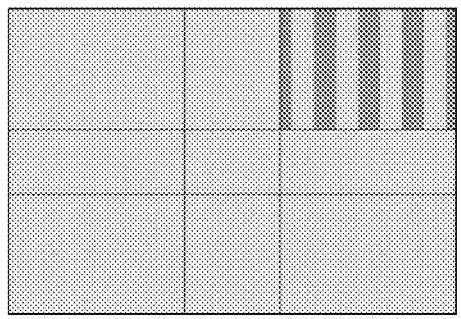
Figure 6F:
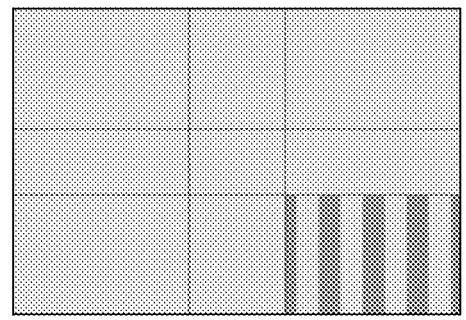
Figure 6G:
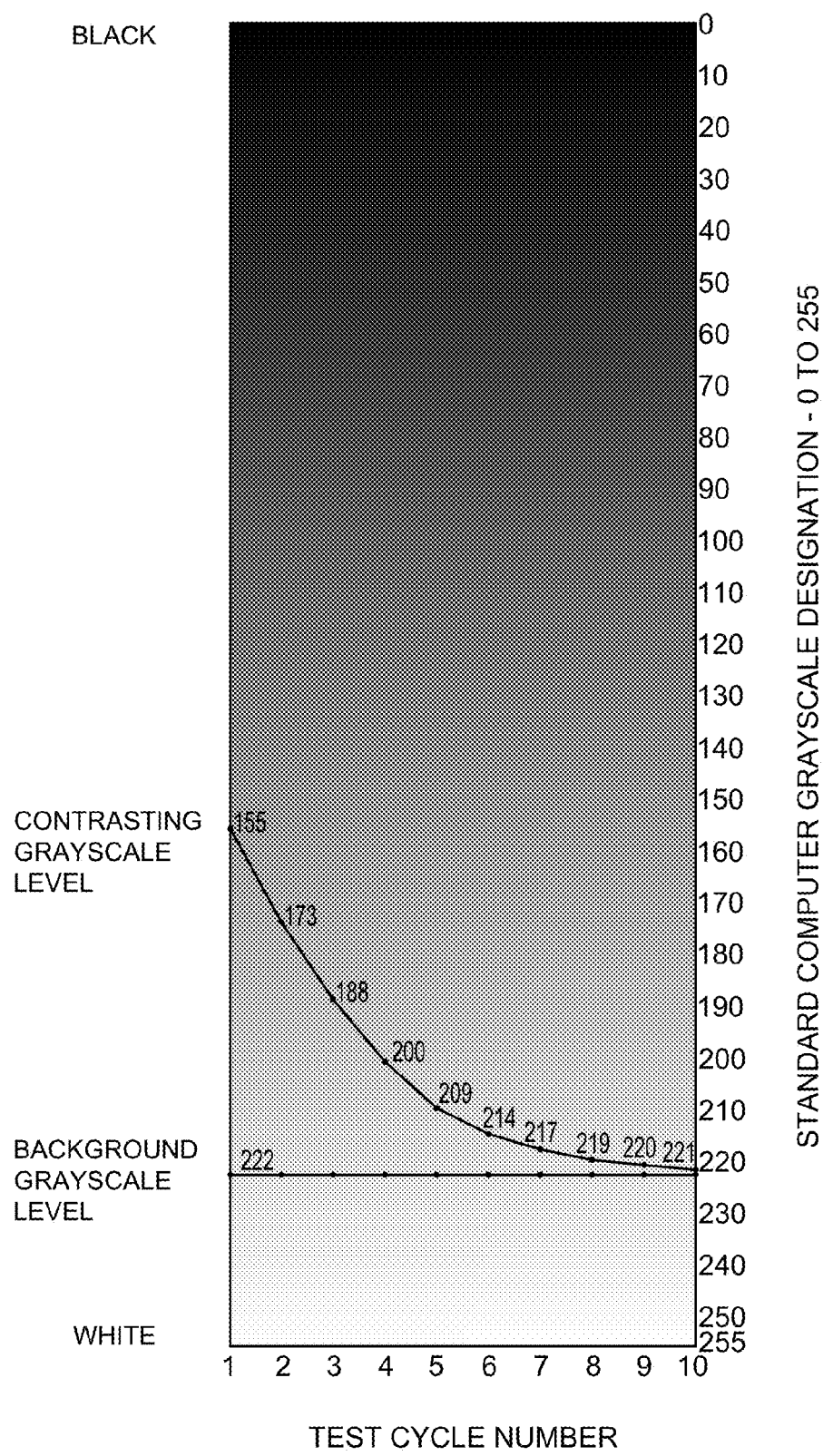
FIG. 6G is a graph showing the progression of decreasing contrast through 10 cycles in this example.

In a fourth example of a test session according to the invention, in which the dark test area appears as a pattern of two contrasting brightnesses, display sets include no letter or other image in test area 5. In addition, as shown in FIG. 6, in the first cycle, one test area will contain two contrasting shades of gray—one darker and one lighter—with the other eight quadrants having that same lighter shade of gray throughout every set in the first cycle (as shown in FIGS. 6A-6F) and in every subsequent cycle of the session (not shown). In this example of the test, the maximum of number cycles is 10. The progression of contrast through the 10 cycles is represented in FIG. 6G, a graph in which the test cycle number is plotted along one axis and brightness according to a standard computer grayscale designation (ranging from 0 for absolute black to 255 for absolute white) is plotted along a second axis. While the background grayscale level remains at 222 for each of the up to 10 cycles, the contrasting grayscale level for each cycle is as presented in Table 1:

TABLE 1

| Test Cycle Number | Contrasting Grayscale Level |
|---|---|
| 1 | 155 |
| 2 | 173 |
| 3 | 188 |
| 4 | 200 |
| 5 | 209 |
| 6 | 214 |
| 7 | 217 |
| 8 | 219 |
| 9 | 220 |
| 10 | 221 |

In this example, the level of contrast in the first cycle is one for which inability of the patient to perceive it will signify that the patient's contrast sensitivity has deteriorated to the degree that further testing will be unlikely to serve any benefit to the patient. The rate of change in contrast is greatest in the early cycles, and least in the later cycles, for the purpose of enabling the test to detect at essentially the earliest instance subtle, but diagnostically significant, changes in the patient's contrast sensitivity over time.

Computer System

FIG. 7 is a flowchart for a computer-based system for administering a contrast sensitivity test according to one embodiment of the invention. Preferably, this embodiment is accessible to operators and test subjects over the World Wide Web via a Web browser.

Preferably, an operator—typically a doctor or technician—will assist a patient to whom the test will be administered. For example, the operator ensures that the patient is positioned in front of a computer monitor appropriately, including the correct distance from the monitor. The operator may also determine if it is possible or desirable for the patient to operate a computer by, for example, clicking a mouse button to provide input to the computer system. If it is not possible or desirable for the patient to do so, the operator may provide instructions to the patient such as these:

"You will see a series of grayscale test panels appear on the screen. In each panel, one of five different areas will be darker than the others. The central area will contain an alphabet letter. Throughout the test, maintain focus on the letter in the central area, even if you think the darkened area is likely to be elsewhere. Say out loud the alphabet letter that will appear in the central area each time a new test screen appears, then tell me which area is the dark area, and I (the operator) will register the result by clicking on that area with the mouse. The letter in the central area may change after a click or it may repeat."

Alternately, if the technician believes that the patient has the capacity, the technician may instruct the patient to click on the test area displayed on the monitor that is dark.

Figure 7A:
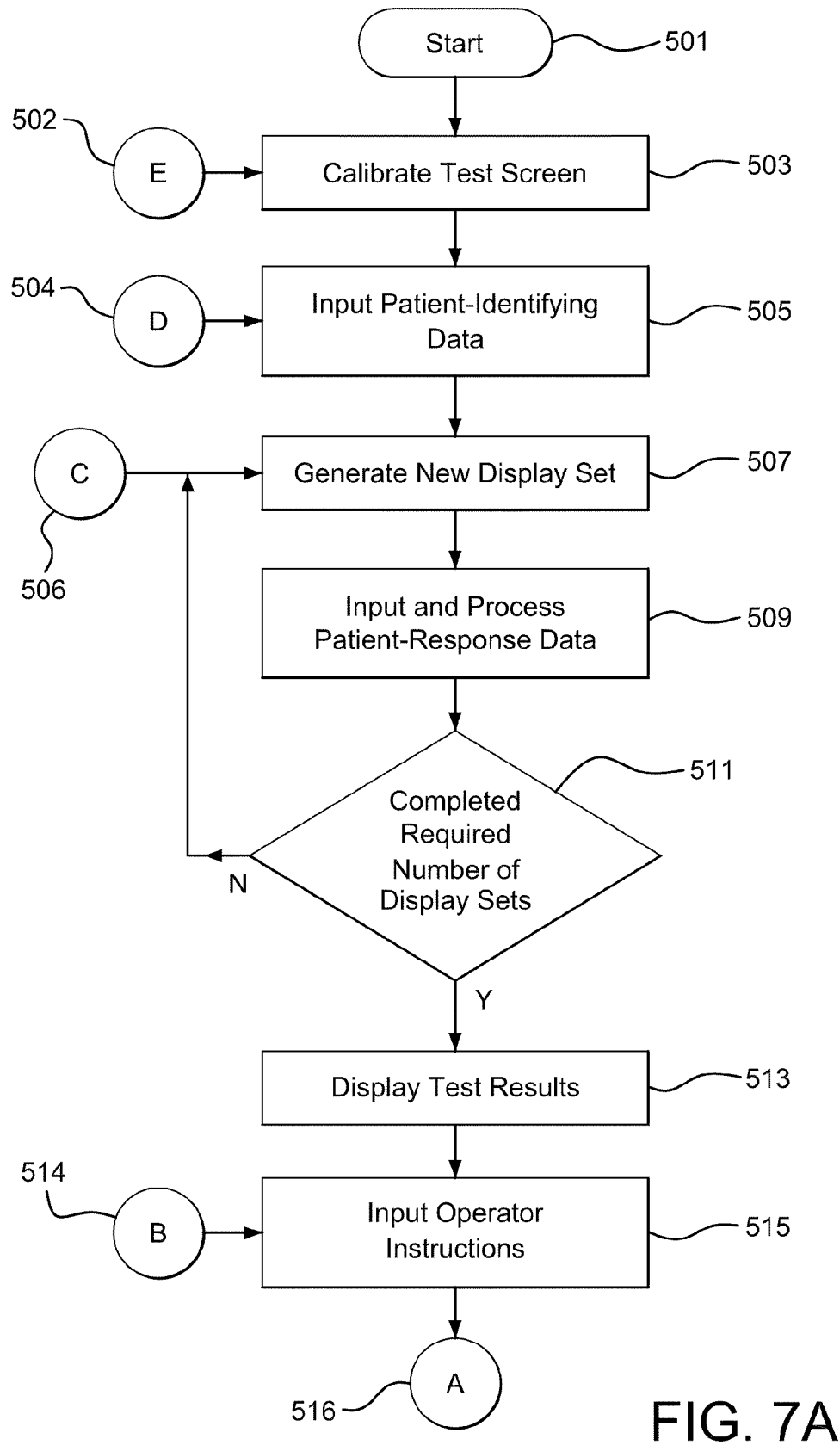
FIGS. 7A-B are a flow chart for a computer-based system for administering a contrast sensitivity test according to one embodiment of the invention.
Figure 7B:
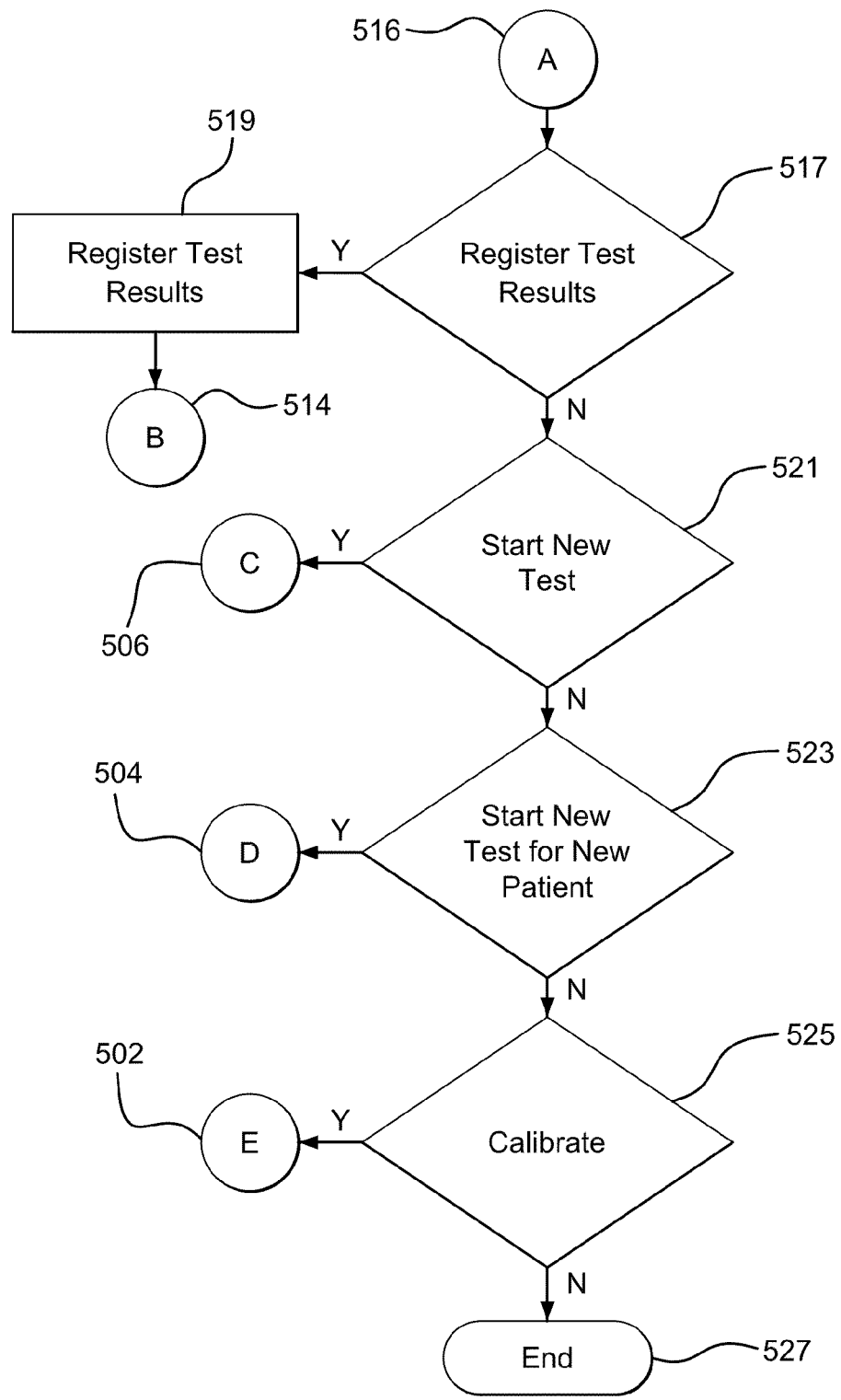

As shown in FIG. 7A, processing by the computer system begins at block 501. The system may require a login by an operator with privileges authorizing the operator to run the system and administer the contrast sensitivity test.

The system at block 503 calibrates a computer screen that will be used to administer test. Preferably, the calibration is initiated by an operator going to a screen-calibration page (e.g., by clicking a Web link) that depicts the display of FIG. 1. The system permits the operator to account for variations in the size and screen resolution of different computer monitors by adjusting the width of the display grid. The screen-calibration page may specify the correct width.

The system at block 505 permits inputting of data identifying a patient to be tested. The computer system preferably includes a central database that can store data, including the patient-identifying data. Instead of entering complete identifying data for a patient, previously entered data may be retrieved (e.g., by the operator entering the patient's name and birth date) from the central database, another data-storage device, or another computer system (e.g., a hospital's computerized patient records).

Figure 2A:
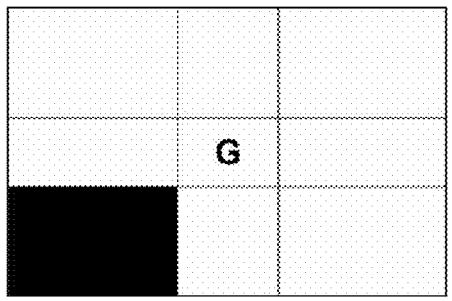
FIGS. 2A-F are computer screenshots depicting an example of a first cycle in a test session according to one embodiment of the invention.
Figure 2B:
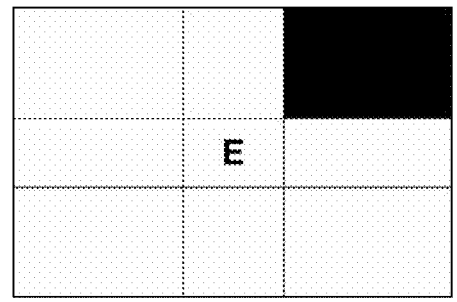
Figure 2C:
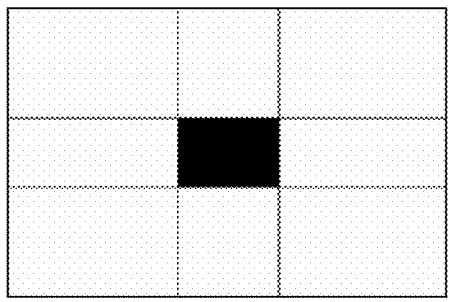
Figure 2D:
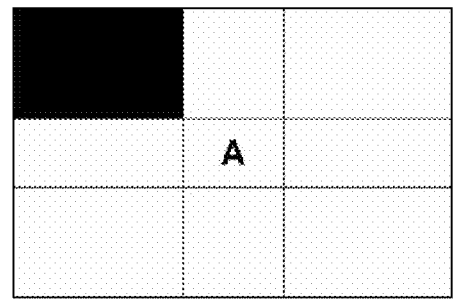
Figure 2E:
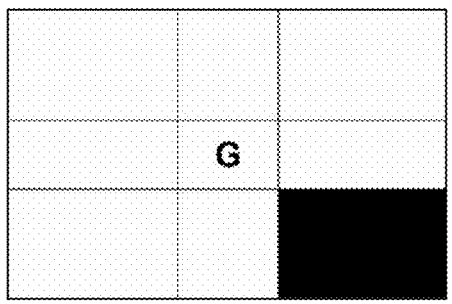
Figure 2F:
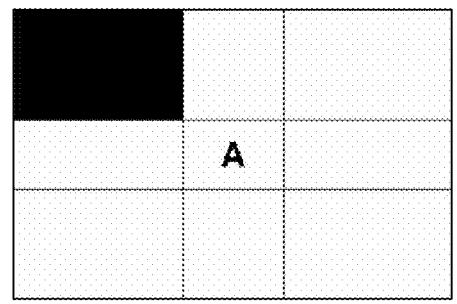
Figure 3A:
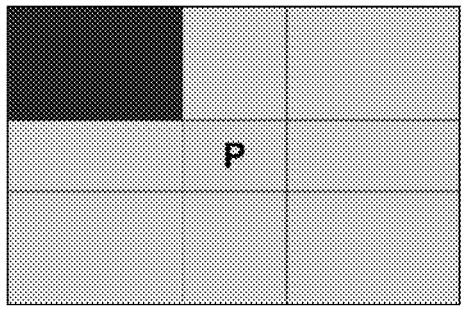
FIGS. 3A-F are computer screenshots depicting an example of a second cycle in the test session according to one embodiment of the invention.
Figure 3B:
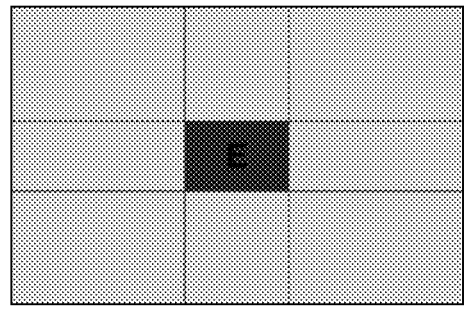
Figure 3C:
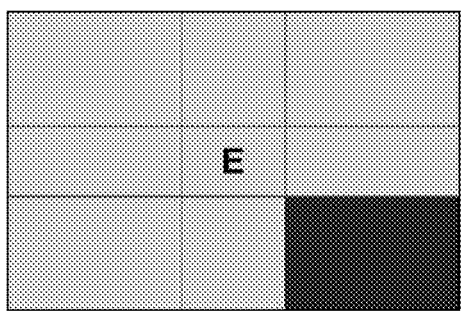
Figure 3D:
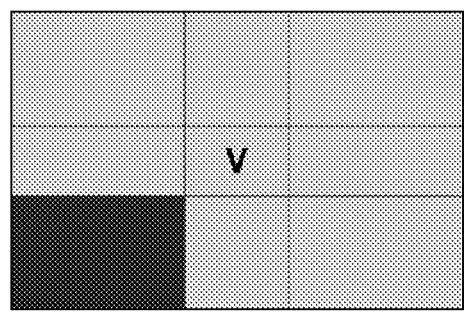
Figure 3E:
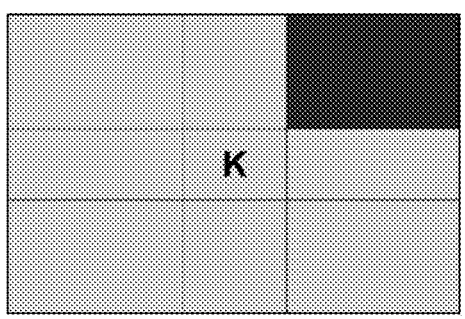
Figure 3F:
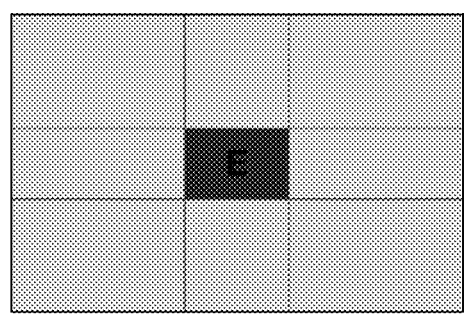
Figure 4A:
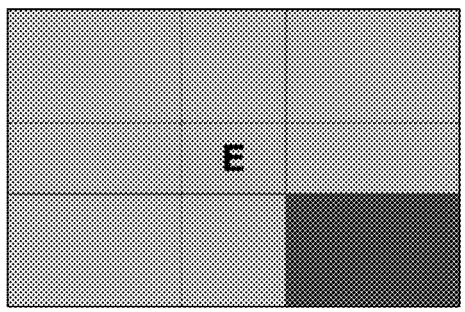
FIGS. 4A-F are computer screenshots depicting an example of a third cycle in the test session according to one embodiment of the invention.
Figure 4B:
Figure 4C:
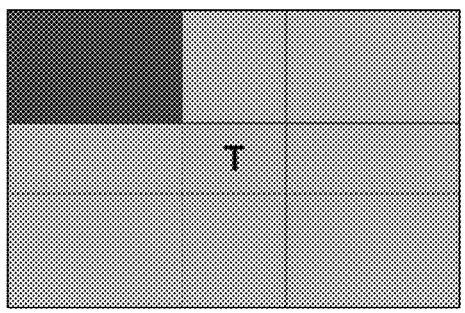
Figure 4D:
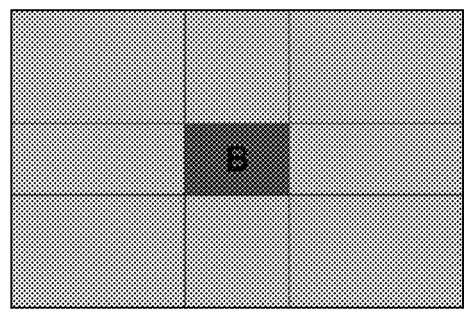
Figure 4E:
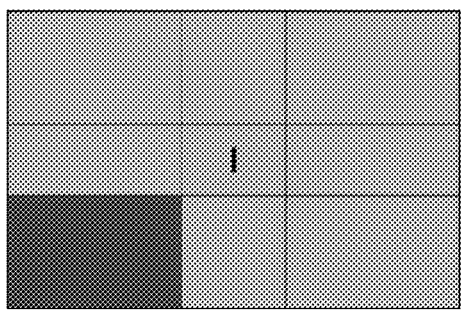
Figure 4F:
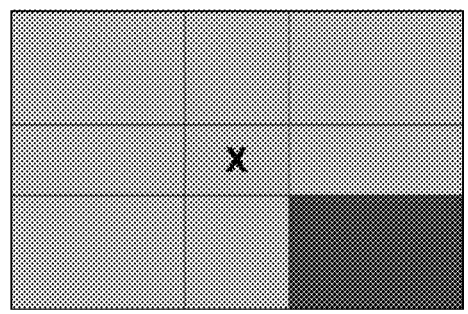
Figure 5A:
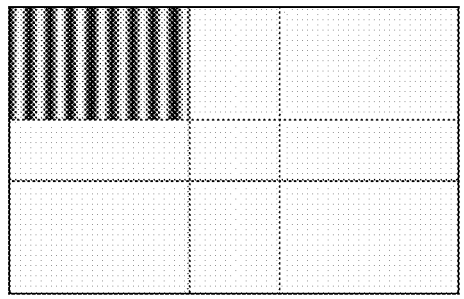
FIGS. 5A-F are computer screenshots depicting an example of a first cycle in a test session according to another embodiment of the invention.
Figure 5B:
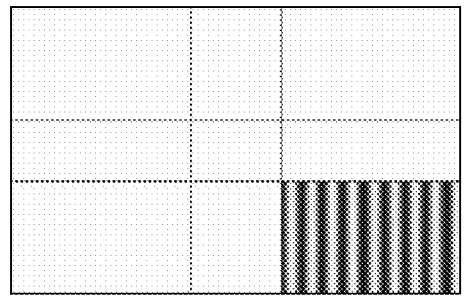
Figure 5C:
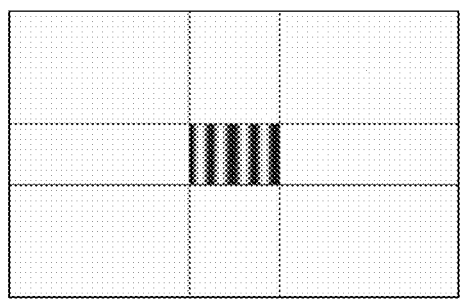
Figure 5D:
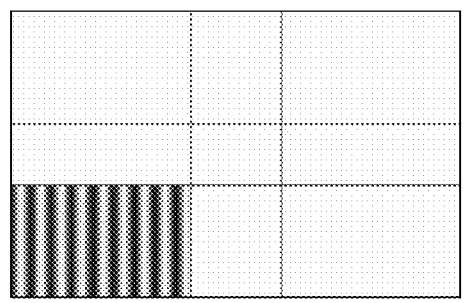
Figure 5E:
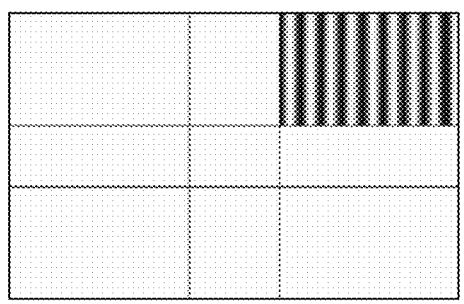
Figure 5F:
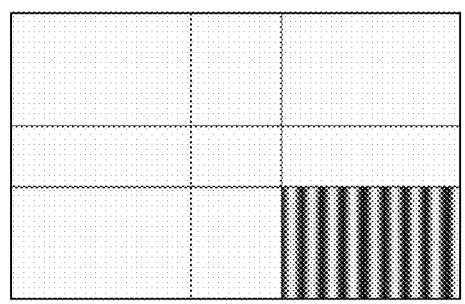

Proceeding to block 507, the system generates a new display set. The system processing indicated at block 507 includes accessing, generating, and keeping track of data as necessary to determine the current cycle and display set. For a test session implemented according to the preferred session described above and depicted partially in FIGS. 2-4, the system will access or generate data on the darkness value for dark test areas, which of test areas 1-4 or test area 5 will be relatively dark, what image will be displayed in test area 5, and any other display data. In this example, when the system first proceeds to block 507 to produce the first display set of the first cycle of the test session, the display set depicted in FIG. 2A is presented to the patient on the computer monitor.

At block 509, the system inputs and processes response data from the patient, indicating which test area the patient perceived to be the dark area. Typically this will be entered by the operator or by the patient.

At block 511, the system determines whether the required number of display sets has been completed. If not, processing returns to block 507; if so, processing continues to block 513, where a summary of the test results is displayed. Preferably this includes a score based on the number of cycles in which the patient answers correctly for all display sets in a cycle. For instance, a patient who provides correct answers for all the display sets in 18 of 20 cycles would receive a score of 90%.

The system next proceeds to block 515 to receive as input operator instructions. When input is received, the system proceeds via jump point A (block 516) to block 517 shown in FIG. 7B.

If at block 517 the system determines the operator input indicated that the test results should be registered, then the system proceeds to block 519 to register the test results (preferably by storing the results in a database on a server computer), and the system then returns via jump point B (block 514) to block 515. Otherwise, the system proceeds to block 521.

If the at block 521 the system determines that operator input indicated that a new test session should be started, then the system proceeds via jump point C (block 506) to block 507. Otherwise, the system proceeds to block 523.

If at block 523 the system determines that the operator input indicated that a new test session for a new patient should be started, then the system proceeds via jump point D (block 504) to block 505. Otherwise, the system proceeds to block 525.

If at block 525 the system determines that the operator input indicated that a calibration be performed, then the system proceeds via jump point E (block 502) to block 503. Otherwise, the system proceeds to block 527 and processing ends.

Example # 5

In another example of a test session according to the invention, up to 20 cycles are possible, but the computer system will not necessarily go through all of them. The system is implemented to provide that, so long as the patient is answering correctly for all the display sets in a cycle, the test progresses at a doubled rate by skipping the next cycle. In this case, the skipped display sets would be counted as "correct" answers.

In this example it is preferable that the system resume presenting every cycle as soon as the patient makes one error during a cycle. It is also preferable that the test session continues until the patient has incorrectly identified, at least once, each of the five test areas, or until the patient reaches the end of the $20^{th}$ cycle.

For instance, let us say that during cycle Nos. 1, 3, and 5 the patient makes no mistakes; during cycle No. 7 the patient incorrectly identifies test area 3; during cycle No. 8 the patient incorrectly identifies test area 5; during cycle No. 9 the patient incorrectly identifies test areas 1, 7, and 9 (in whatever order). In this example, the test session will end after cycle No. 9 is completed; cycle Nos. 1-6 will be scored as correct, and cycle Nos. 7-20 will be scored as incorrect, for a final score of 6 out of 20 (30%).

Taking another instance, in which the patient makes no mistakes until the $13^{th}$ cycle: let us say that the patient first makes a mistake concerning test area 1 during the $13^{th}$ cycle, then makes mistakes concerning test areas 1 and 5 (in either order) during the $14^{th}$ cycle, and then make mistakes concerning test areas 1, 3, 5, 7, and 9 (in whatever order) during the $15^{th}$ cycle. In this case, by the end of the test session the patient will have been presented with cycle Nos. 1, 3, 5, 7, 9, 11, 13, 14, and 15. For this patient, 12 answers would be scored correct for cycle Nos. 1-12, and 8 answers would be scored incorrect for cycle Nos. 13-20, for a final score of 12 out of 20 (60%).

It is preferred in this example that the last four cycles (Nos. 17-20) will always be presented—i.e., that the doubled rate ends once the patient begins cycle No. 17—so long as mistakes have not been made for all five test areas. For instance, a patient who makes no mistakes throughout the entire test session will have been presented with cycle Nos. 1, 3, 5, 7, 9, 11, 13, 15, 17, 18, 19, and 20. For another instance, a patient who makes no mistakes through the $17^{th}$ cycle, then makes mistakes concerning test areas 1, 3, 5, and 7 (in whatever order) during the $18^{th}$ cycle, and then makes a mistake concerning test area 9 during the $19^{th}$ cycle, the patient will have been presented with cycle Nos. 1, 3, 5, 7, 9, 11, 13, 15, 17, 18, and 19.

In this example of a test session, whether a patient's answer is correct or incorrect is preferably determined as follows. In a given display set, if the patient responds by identifying as dark a test area that is not in fact the dark test area, the next display set in that cycle will repeat the set just presented. If the patient fails again to correctly identify the dark test area, the display set is registered as incorrectly answered. If on the second presentation of the same display set the patient correctly identifies the dark test area, then the same set appears a third time, and the patient's third click defines the set as correct or incorrect. It is still the case that five different display sets and a sixth, dummy set is presented during the cycle, although each of the six display sets could be presented up to three times.

Example # 6

In another example of a test session according to the invention, up to 10 cycles are possible. So long as the patient is answering correctly for all the display sets in a cycle, the test progresses at a doubled rate by skipping the next cycle, but cycle Nos. 6-10 are always presented, so long as there is at least one test area that the patient has not yet mistaken. In addition, if the patient makes a mistake during one cycle that follows a skipped cycle, the test proceeds to complete that one cycle and then regresses to the skipped cycle.

For instance, a patient who makes no mistakes in cycle No. 1 is presented next with cycle No. 3. If no mistakes are made, the patient is then presented with cycle No. 5. Let us say that here the patient makes a mistake concerning test area 7; test area 7 in cycle No. 5 is then scored as incorrect and the patient is presented with cycle No. 4. If, say, the patient makes a mistake concerning test area 1, then test area 1 in cycle No. 4 is scored as incorrect. The patient is then presented with a second instance of cycle No. 5. Whatever the patient's responses, test area 7 in cycle No. 5 remains scored as incorrect. Let us say that the patient again makes a mistake concerning only test area 7. The patient is then presented with cycle Nos. 6-10. Let us say that no mistake is made until cycle No. 10, when the patient makes mistakes concerning test areas 1, 3, and 9 (in whatever order), and the patient makes no mistake throughout the test session for test area 5.

The score for any test area equals the lowest cycle number in which a mistake occurred for that test area, minus 1, times 2. For a test area where no mistake is made, the score is 20 (10 times 2). (Multiplication by 2 provides that the highest possible test score will be 100.) Scoring in this example is shown in Table 2. Adding the scores for the five test areas, for this patient the final score is 70 (or 70%).

TABLE 2

| Test Area Number | Lowest Cycle Number of Mistake | Score |
|---|---|---|
| 1 | 4 | 6 |
| 3 | 10 | 18 |
| 5 | N/A | 20 |
| 7 | 5 | 8 |
| 9 | 10 | 18 |

As those skilled in the art will recognize, numerous variations are possible for many aspects of the invention, such as the appearance of the contrasting quadrants, the number of cycles, the number of display sets, the sequence in which display sets are presented, whether and when display sets are repeated, the way that contrast between test areas is displayed, whether there is contrast between nontest areas or between test and nontest areas, how correct or incorrect answers are determined, the score or measurement of contrast sensitivity based upon data from the test session, and the way that operator or patient input is received. In particular, contrast between any one or more quadrants with any other one or more quadrants can be achieved in a variety of ways. The examples described here—including a test area that appears as a solid, as a pattern such as vertical bars, or as an animation such as a sinusoidal frequency grating—are merely illustrative. A computer system according to the invention may be implemented using a variety of hardware (including processors, memories, storage devices, and storage media), software (including operating systems, databases, and Web-based applications), configurations (including a single unit, multiple units, networks, and client/server arrangements), and other elements. The scope of the invention is defined by the claims.

The invention claimed is:
1. A method for measuring contrast sensitivity comprising:
 (a) presenting to a person a test pattern having a plurality of test areas;
 (b) providing that one of the test areas contrasts with the other test areas;
 (c) receiving a response from the person indicating which test area the person perceives as contrasting with the other test areas;
 (d) repeating steps (b) and (c) a first predetermined number of times, each time providing that another test area contrasts with the other test areas; and
 (e) repeating steps (b), (c), and (d) a second predetermined number of times, each first time that step (b) is carried out decreasing the contrast that appears between the test areas.
2. The method of claim 1, wherein in step (b) the one of the test areas appears as a solid.
3. The method of claim 1, wherein in step (b) the one of the test areas appears as a pattern.
4. The method of claim 3, wherein the pattern is a plurality of contrasting brightnesses.
5. The method of claim 1, wherein in step (b) the one of the test areas appears as an animation.
6. The method of claim 5, wherein the animation is a sinusoidal frequency grating.
7. A method for measuring contrast sensitivity comprising:
 (a) presenting to a person a test pattern having a plurality of test and nontest areas;
 (b) providing that one of the test areas contrasts with the other test and nontest areas;
 (c) receiving a response from the person indicating which test area the person perceives as contrasting with the other test and nontest areas;
 (d) repeating steps (b) and (c) a first predetermined number of times, each time providing that another test area contrasts with the other test and nontest areas; and
 (e) repeating steps (b), (c), and (d) a second predetermined number of times, each first time that step (b) is carried out decreasing the contrast that appears between one of the test areas and the other test and nontest areas.
8. A method for measuring contrast sensitivity comprising:
 (a) presenting to a person a test pattern including five test areas;
 (b) providing that one of the test areas contrasts with the other four test areas;
 (c) receiving a response from the person indicating which test area the person perceives as contrasting with the other test areas;
 (d) repeating steps (b) and (c) at least four more times, each time providing that another test area contrasts with the other test areas and that no test area repeats as the contrasting test area; and
 (e) repeating steps (b), (c), and (d) up to 20 times, each first time that step (b) is carried out decreasing the contrast that appears between the test areas.
9. The method of claim 8, wherein four of the test areas are disposed around the fifth test area.

10. The method of claim 8, wherein the test pattern is a 3 by 3 matrix, and:
- (a) in row 1, columns 1 and 3 are test areas and column 2 is a nontest area;
- (b) in row 2, column 2 is a test area and columns 1 and 3 are nontest areas; and
- (c) in row 3, columns 1 and 3 are test areas and column 2 is a nontest area.

11. A method for measuring contrast sensitivity comprising:
- (a) presenting to a person a test pattern having a plurality of test areas;
- (b) providing that one of the test areas has a first brightness and that the other test areas have a second brightness, wherein the first brightness is darker than the second brightness;
- (c) receiving a response from the person indicating which test area the person perceives as darker than the other test areas;
- (d) repeating steps (b) and (c) a first predetermined number of times, each time providing that another test area is darker than the remaining test areas; and
- (e) repeating steps (b), (c), and (d) a second predetermined number of times, each time decreasing the contrast between the darker test area and the other test areas.

12. A method for measuring contrast sensitivity comprising:
- (a) presenting to a person a test pattern including a 3 by 3 matrix, wherein
  - (i) in row 1, columns 1 and 3 are test areas and column 2 is a nontest area;
  - (ii) in row 2, column 2 is a test area and columns 1 and 3 are nontest areas; and
  - (iii) in row 3, columns 1 and 3 are test areas and column 2 is a nontest area;
- (b) providing an image for use as a fixation point in the test area of row 2, column 2;
- (c) providing that one of the test areas is relatively dark and that the other four test areas are relatively light;
- (d) receiving a response from the person indicating which test area the person perceives as darker than the other test areas;
- (e) repeating steps (b), (c), and (d) four more times, each time providing in step (c) that another test area is dark and that the remaining four test areas are light and that no test area repeats as the dark test area;
- (f) repeating steps (b), (c), (d), and (e) up to 20 more times, each first time that step (c) is performed decreasing the contrast between the relatively dark test area and the other four test areas; and
- (g) calculating a score based on the received responses.

13. A method for measuring contrast sensitivity comprising:
- (a) presenting to a person a test pattern including a 3 by 3 matrix, wherein
  - (i) in row 1, columns 1 and 3 are test areas and column 2 is a nontest area;
  - (ii) in row 2, column 2 is a test area and columns 1 and 3 are nontest areas; and
  - (iii) in row 3, columns 1 and 3 are test areas and column 2 is a nontest area;
- (b) defining a display set and presenting it to the person, wherein the display set includes:
  - (i) an image for use as a fixation point in the test area of row 2, column 2; and
  - (ii) one of the test areas being relatively dark and that the other four test areas being relatively light;
- (c) receiving a first response from the person indicating which test area the person perceives as darker than the other test areas;
- (d) repeating steps (b) and (c) four more times, each time providing in the display set defined in step (b) that another test area is relatively dark and that the remaining four test areas are relatively light and that no test area repeats as the dark test area;
- (e) presenting to the person one of the display sets previously defined;
- (f) repeating steps (b), (c), (d), and (e) up to 20 more times, each first time that step (b) is performed decreasing the contrast between the dark test area and the other four test areas; and
- (g) calculating a score based on the received responses.

14. The method of claim 13, wherein in step (e) the one of the display sets previously defined is presented with a different image in the test area of row 2, column 2.

15. A memory storing instructions adapted to be executed by a computer processor to perform a method for measuring contrast sensitivity comprising:
- (a) presenting to a person a test pattern having a plurality of test areas;
- (b) providing that one of the test areas contrasts with the other test areas;
- (c) receiving a response from the person indicating which test area the person perceives as contrasting with the other test areas;
- (d) repeating steps (b) and (c) a first predetermined number of times, each time providing that another test area contrasts with the other test areas; and
- (e) repeating steps (b), (c), and (d) a second predetermined number of times, each first time that step (b) is carried out decreasing the contrast that appears between the test areas.

16. The memory of claim 15, wherein in step (b) the one of the test areas appears as a solid.

17. The memory of claim 15, wherein in step (b) the one of the test areas appears as a pattern.

18. The memory of claim 17, wherein the pattern is a plurality of contrasting brightnesses.

19. The memory of claim 15, wherein in step (b) the one of the test areas appears as an animation.

20. The memory of claim 19, wherein the animation is a sinusoidal frequency grating.

21. A memory storing instructions adapted to be executed by a computer processor to perform a method for measuring contrast sensitivity comprising:
- (a) presenting to a person a test pattern having a plurality of test and nontest areas;
- (b) providing that one of the test areas contrasts with the other test and nontest areas;
- (c) receiving a response from the person indicating which test area the person perceives as contrasting with the other test and nontest areas;
- (d) repeating steps (b) and (c) a first predetermined number of times, each time providing that another test area contrasts with the other test and nontest areas; and
- (e) repeating steps (b), (c), and (d) a second predetermined number of times, each first time that step (b) is carried out decreasing the contrast that appears between one of the test areas and the other test and nontest areas.

22. A memory storing instructions adapted to be executed by a computer processor to perform a method for measuring contrast sensitivity comprising:
- (a) presenting to a person a test pattern including five test areas;

(b) providing that one of the test areas contrasts with the other four test areas;

(c) receiving a response from the person indicating which test area the person perceives as contrasting with the other test areas;

(d) repeating steps (b) and (c) at least four more times, each time providing that another test area contrasts with the other test areas and that no test area repeats as the contrasting test area; and (e) repeating steps (b), (c), and (d) up to 20 times, each first time that step (b) is carried out decreasing the contrast that appears between the test areas.

23. The memory of claim 22, wherein four of the test areas are disposed around the fifth test area.

24. The memory of claim 22; wherein the test pattern is a 3 by 3 matrix, and:

(a) in row 1, columns 1 and 3 are test areas and column 2 is a nontest area;

(b) in row 2, column 2 is a test area and columns 1 and 3 are nontest areas; and (c) in row 3, columns 1 and 3 are test areas and column 2 is a nontest area.

25. A memory storing instructions adapted to be executed by a computer processor to perform a method for measuring contrast sensitivity comprising:

(a) presenting to a person a test pattern having a plurality of test areas;

(b) providing that one of the test areas has a first brightness and that the other test areas have a second brightness, wherein the first brightness is darker than the second brightness;

(c) receiving a response from the person indicating which test area the person perceives as darker than the other test areas;

(d) repeating steps (b) and (c) a first predetermined number of times, each time providing that another test area is darker than the remaining test areas; and (e) repeating steps (b), (c), and (d) a second predetermined number of times, each time decreasing the contrast between the darker test area and the other test areas.

26. A memory storing instructions adapted to be executed by a computer processor to perform a method for measuring contrast sensitivity comprising:

(a) presenting to a person a test pattern including a 3 by 3 matrix, wherein (i) in row 1, columns 1 and 3 are test areas and column 2 is a nontest area;

(ii) in row 2, column 2 is a test area and columns 1 and 3 are nontest areas; and (iii) in row 3, columns 1 and 3 are test areas and column 2 is a nontest area;

(b) providing an image for use as a fixation point in the test area of row 2, column 2;

(c) providing that one of the test areas is relatively dark and that the other four test areas are relatively light;

(d) receiving a response from the person indicating which test area the person perceives as darker than the other test areas;

(e) repeating steps (b), (c), and (d) four more times, each time providing in step (c) that another test area is dark and that the remaining four test areas are light and that no test area repeats as the dark test area;

(f) repeating steps (b), (c), (d), and (e) up to 20 more times, each first time that step (c) is performed decreasing the contrast between the relatively dark test area and the other four test areas; and (g) calculating a score based on the received responses.

27. A memory storing instructions adapted to be executed by a computer processor to perform a method for measuring contrast sensitivity comprising:

(a) presenting to a person a test pattern including a 3 by 3 matrix, wherein (i) in row 1, columns 1 and 3 are test areas and column 2 is a nontest area;

(ii) in row 2, column 2 is a test area and columns 1 and 3 are nontest areas; and (iii) in row 3, columns 1 and 3 are test areas and column 2 is a nontest area;

(b) defining a display set and presenting it to the person, wherein the display set includes:

(i) an image for use as a fixation point in the test area of row 2, column 2; and (ii) one of the test areas being relatively dark and that the other four test areas being relatively light;

(c) receiving a first response from the person indicating which test area the person perceives as darker than the other test areas;

(d) repeating steps (b) and (c) four more times, each time providing in the display set defined in step (b) that another test area is relatively dark and that the remaining four test areas are relatively light and that no test area repeats as the dark test area;

(e) presenting to the person one of the display sets previously defined;

(f) repeating steps (b), (c), (d), and (e) up to 20 more times, each first time that step (b) is performed decreasing the contrast between the dark test area and the other four test areas; and (g) calculating a score based on the received responses.

28. The memory of claim 27, wherein in step (e) the one of the display sets previously defined is presented with a different image in the test area of row 2, column 2.

29. A computer-implemented apparatus for measuring contrast sensitivity comprising:

a memory;

a computer processor in communication with the memory, the computer processor executing functions comprising:

(a) presenting to a person a test pattern having a plurality of test areas;

(b) providing that one of the test areas contrasts with the other test areas;

(c) receiving a response from the person indicating which test area the person perceives as contrasting with the other test areas;

(d) repeating steps (b) and (c) a first predetermined number of times, each time providing that another test area contrasts with the other test areas; and (e) repeating steps (b), (c), and (d) a second predetermined number of times, each first time that step (b) is carried out decreasing the contrast that appears between the test areas.

30. The apparatus of claim 29, wherein in function (b) the one of the test areas appears as a solid.

31. The apparatus of claim 29, wherein in function (b) the one of the test areas appears as a pattern.

32. The apparatus of claim 31, wherein the pattern is a plurality of contrasting brightnesses.

33. The apparatus of claim 29, wherein in function (b) the one of the test areas appears as an animation.

34. The apparatus of claim 33, wherein the animation is a sinusoidal frequency grating.

35. A computer-implemented apparatus for measuring contrast sensitivity comprising:
- a memory;
- a computer processor in communication with the memory, the computer processor executing functions comprising:
  - (a) presenting to a person a test pattern having a plurality of test and nontest areas;
  - (b) providing that one of the test areas contrasts with the other test and nontest areas;
  - (c) receiving a response from the person indicating which test area the person perceives as contrasting with the other test and nontest areas;
  - (d) repeating functions (b) and (c) a first predetermined number of times, each time providing that another test area contrasts with the other test and nontest areas; and
  - (e) repeating functions (b), (c), and (d) a second predetermined number of times, each first time that function (b) is carried out decreasing the contrast that appears between one of the test areas and the other test and nontest areas.

36. A computer-implemented apparatus for measuring contrast sensitivity comprising:
- a memory;
- a computer processor in communication with the memory, the computer processor executing functions comprising:
  - (a) presenting to a person a test pattern including five test areas;
  - (b) providing that one of the test areas contrasts with the other four test areas;
  - (c) receiving a response from the person indicating which test area the person perceives as contrasting with the other test areas;
  - (d) repeating functions (b) and (c) at least four more times, each time providing that another test area contrasts with the other test areas and that no test area repeats as the contrasting test area; and
  - (e) repeating functions (b), (c), and (d) up to 20 times, each first time that function (b) is carried out decreasing the contrast that appears between the test areas.

37. The apparatus of claim 36, wherein four of the test areas are disposed around the fifth test area.

38. The apparatus of claim 36, wherein the test pattern is a 3 by 3 matrix, and:
- (a) in row 1, columns 1 and 3 are test areas and column 2 is a nontest area;
- (b) in row 2, column 2 is a test area and columns 1 and 3 are nontest areas; and
- (c) in row 3, columns 1 and 3 are test areas and column 2 is a nontest area.

39. A computer-implemented apparatus for measuring contrast sensitivity comprising:
- a memory;
- a computer processor in communication with the memory, the computer processor executing functions comprising:
  - (a) presenting to a person a test pattern having a plurality of test areas;
  - (b) providing that one of the test areas has a first brightness and that the other test areas have a second brightness, wherein the first brightness is darker than the second brightness;
  - (c) receiving a response from the person indicating which test area the person perceives as darker than the other test areas;
  - (d) repeating functions (b) and (c) a first predetermined number of times, each time providing that another test area is darker than the remaining test areas; and
  - (e) repeating functions (b), (c), and (d) a second predetermined number of times, each time decreasing the contrast between the darker test area and the other test areas.

40. A computer-implemented apparatus for measuring contrast sensitivity comprising:
- a memory;
- a computer processor in communication with the memory, the computer processor executing functions comprising:
  - (a) presenting to a person a test pattern including a 3 by 3 matrix, wherein
    - (i) in row 1, columns 1 and 3 are test areas and column 2 is a nontest area;
    - (ii) in row 2, column 2 is a test area and columns 1 and 3 are nontest areas; and
    - (iii) in row 3, columns 1 and 3 are test areas and column 2 is a nontest area;
  - (b) providing an image for use as a fixation point in the test area of row 2, column 2;
  - (c) providing that one of the test areas is relatively dark and that the other four test areas are relatively light;
  - (d) receiving a response from the person indicating which test area the person perceives as darker than the other test areas;
  - (e) repeating functions (b), (c), and (d) four more times, each time providing in function (c) that another test area is dark and that the remaining four test areas are light and that no test area repeats as the dark test area;
  - (f) repeating functions (b), (c), (d), and (e) up to 20 more times, each first time that function (c) is performed decreasing the contrast between the relatively dark test area and the other four test areas; and
  - (g) calculating a score based on the received responses.

41. A computer-implemented apparatus for measuring contrast sensitivity comprising:
- a memory;
- a computer processor in communication with the memory, the computer processor executing functions comprising:
  - (a) presenting to a person a test pattern including a 3 by 3 matrix, wherein
    - (i) in row 1, columns 1 and 3 are test areas and column 2 is a nontest area;
    - (ii) in row 2, column 2 is a test area and columns 1 and 3 are nontest areas; and
    - (iii) in row 3, columns 1 and 3 are test areas and column 2 is a nontest area;
  - (b) defining a display set and presenting it to the person, wherein the display set includes:
    - (i) an image for use as a fixation point in the test area of row 2, column 2; and
    - (ii) one of the test areas being relatively dark and that the other four test areas being relatively light;
  - (c) receiving a first response from the person indicating which test area the person perceives as darker than the other test areas;
  - (d) repeating functions (b) and (c) four more times, each time providing in the display set defined in function (b) that another test area is relatively dark and that the remaining four test areas are relatively light and that no test area repeats as the dark test area;
  - (e) presenting to the person one of the display sets previously defined;
  - (f) repeating functions (b), (c), (d), and (e) up to 20 more times, each first time that function (b) is performed decreasing the contrast between the dark test area and the other four test areas; and
  - (g) calculating a score based on the received responses.

42. The apparatus of claim 41, wherein in function (e) the one of the display sets previously defined is presented with a different image in the test area of row 2, column 2.

* * * * *

UNITED STATES PATENT AND TRADEMARK OFFICE
Certificate

Patent No. 8,042,946 B1                                                            Patented: October 25, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: George L. Spaeth, Philadelphia, PA (US); Jesse Richman, Providence, RI (US); and Eric E. Spaeth, Philadelphia, PA (US).

Signed and Sealed this Twenty-ninth Day of July 2014.

*RICKY L. MACK*
*Supervisory Patent Examiner*
*Art Unit 2872*
*Technology Center 2800*